United States Patent [19]

Irikura

[11] 4,007,201
[45] Feb. 8, 1977

[54] NOVEL PYRAZOLE DERIVATIVES

[75] Inventor: Tsutomu Irikura, Tokyo, Japan

[73] Assignee: Kyorin Pharmaceutical Co. Ltd., Tokyo, Japan

[22] Filed: May 30, 1975

[21] Appl. No.: 582,268

[52] U.S. Cl. .......................... 260/310 R; 424/273
[51] Int. Cl.² ............ C07D 231/12; A61K 31/415
[58] Field of Search ................ 260/310 R; 424/273

[56] References Cited

UNITED STATES PATENTS 3,887,709   6/1975   Brzozowski et al. ............. 424/273

*Primary Examiner*—Donald B. Moyer
*Attorney, Agent, or Firm*—Armstrong, Nikaido & Wegner

[57] ABSTRACT

The present invention relates to novel compounds of pyrazole derivatives, which are useful as antidiabetic agents, and to processes for producing the same.

5 Claims, 1 Drawing Figure

NOVEL PYRAZOLE DERIVATIVES

DETAILED DESCRIPTION OF THIS INVENTION:

Figure 1:
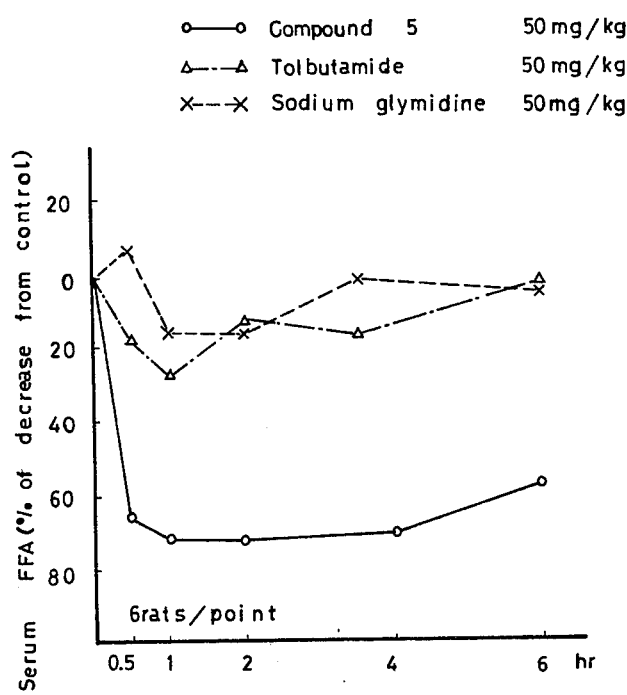

The present invention relates to a compound of the general formula [II],

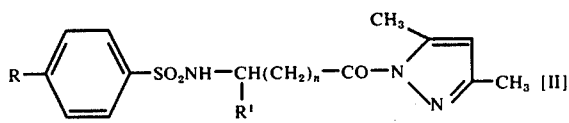

(in which R represents 2-acetaminoethyl, 2-ethyoxycarbonyl-aminoethyl, 2-(2-methoxy-5-chlorobenzoylamino)ethyl, 2-(2-pyrazinecarbonylamino)ethyl, isobutyl, cyclohexyl group or chlorine atom; n is 0 or 1 when $R^1$ represents hydrogen atom; n is 0 when $R^1$ represents methyl, phenyl, or benzyl group), and to processes for producing the same. According to the present invention, the useful compounds as antidiabetic agents can be prepared as follows. Namely, a compound of the general formula [I]:

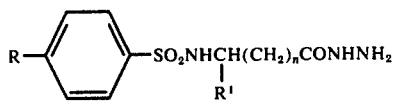

(in which R represents 2-acetaminoethyl, 2-ethoxycarbonyl-aminoethyl, 2-(2-methoxy-5-chlorobenzoylamino)ethyl, 2-(2-pyrazinecarbonylamino)ethyl, isobutyl, cyclohexyl group or chlorine atom; n is 0 or 1 when $R^1$ represents hydrogen atom; n is 0 when $R^1$ represents methyl, phenyl, or benzyl group), may be reacted with equimolar or excess quantities of acetylacetone in an appropriate solvent such as, for example, a class of alcohol and so on, and ring closure undergoes very smoothly to provide a pyrazole derivative having the general formula [II]:

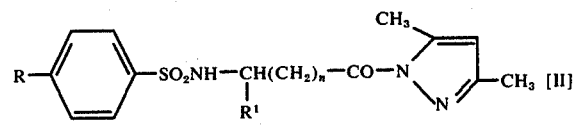

(in which R, $R^1$, and n representation are the same as above). This reaction often proceeds readily on addition of trace amounts of acetic acid. Sometimes acetic acid is very suitable for a reaction solvent.

These new compounds of the present invention are very useful as anti-diabetic agents, which is supported from the following pharmacological studies. The animals used for the pharmacological studies were male Sprague Dawley rats except otherwise noted.

1. Hypoglycemic activity in non-diabetic rats (screening test)

The rats were fasted for 16 – 18 hours prior to the experiment and those weighing 140 – 160g were used. Glucose solution (100 mg/0.5ml/150g body weight) was subcutaneously injected on the fasted rats. Each of the present compounds was suspended in 1% carboxymethyl cellulose (CMC), and about 0.5 ml of the suspension (corresponding to 100 mg/kg of the compound per body weight) was orally administered. Blood samples were taken from the tail vein of the rats at 2 and 5 hours after the administration, and the blood glucose level in each sample (0.1 ml) was determined by the micro method of Momose as described in SOGO-RIN-SHO 11, 120 (1962).

Summary of the method of Momose is as follow.

Principle 3,5-Dinitrophthalic acid is reduced with glucose to stable orange-red azo-compound via red hydroxyaminophthalic acid in basic media.

Method

1. Deproteinization

To 0.5ml of water was added 0.1ml of blood and shaken to hemolyze, and to which was added 1.7ml of 0.06N barium hydroxide solution. To the resulting dark-brown solution was added 1.7ml of zinc sulfate solution (1g/dl), and which was shaken thoroughly and allowed to stand for 2–3min followed by centrifugation.

2. Color development i. Sample

One ml of 3,5-dinitrophthalic acid solution (1.5g of monopyridinium-3,5-dinitrophthalate in 500ml of water) and 1 ml of sodium carbonatesodium hyposulfite solution (125–25g/500ml) were added to 2ml of spernatant solution. The solution was heated at 100° C for 10 min. After cooling with running water for 3 min, water was added to make 20ml.

ii. Reference

To 2ml of water were added 3,5-dinitrophthalic acid solution and an alkaline solution, and the solution was treated as mentioned above.

3. Colorimetry

As the absorbance of reference at 450nm was adjusted to 0, the absorbance of sample corresponded to blood glucose level.

The results were shown in Table 1, which exhibited the effectiveness of the compounds of the present invention.

Table 1

Reducing effects of the compounds of the present invention on the blood glucose level in non-diabetic rats

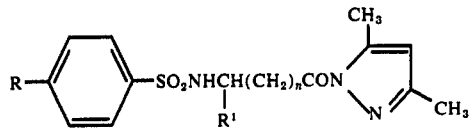

| Compounds | | R | $R^1$ | n | Reduction % of blood glucose from control after 2 hours | after 5 hours |
|---|---|---|---|---|---|---|
| Example | 1 | H | H | 1 | 22.1* | 19.8 |
| " | 2 | $CH_3CONHCH_2CH_2$ | H | 1 | 37.1** | 26.0** |

Table 1-continued

Reducing effects of the compounds of the present invention on
the blood glucose level in non-diabetic rats

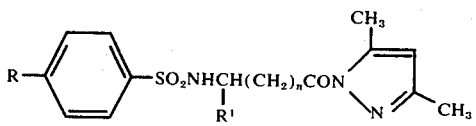

| Compounds | R | R¹ | n | Reduction % of blood glucose from control after 2 hours | after 5 hours |
|---|---|---|---|---|---|
| " | 3  [pyrazinyl]-CONHCH$_2$CH$_2$ | H | 1 | 41.7 | 25.7 |
| " | 4  Cl | H | 0 | 41.9** | 25.2** |
| " | 5  CH$_3$CONHCH$_2$CH$_2$ | H | 0 | 35.2** | 34.1** |
| " | 6  C$_2$H$_5$OCONHCH$_2$CH$_2$ | H | 0 | 33.3** | 22.1** |
| " | 7  C$_2$H$_5$OCONHCH$_2$CH$_2$ | H | 1 | 41.6** | 23.3** |
| " | 8  Cl | H | 1 | 42.5** | 22.1** |
| " | 9  Cl [2-Cl, 3-OCH$_3$ phenyl]-CONHCH$_2$CH$_2$ | H | 0 | 48.1** | 17.7** |
| " | 10 [phenyl]-H | H | 0 | 42.1 | 3.3 |
| " | 11 (CH$_3$)$_2$CHCH$_2$ | H | 0 | 37.9 | 1.4 |
| " | 12 Cl | C$_6$H$_5$ | 0 | 32.6 | 4.0 |
| " | 13 Cl | CH$_3$ | 0 | 51.3 | 5.0 |
| " | 14 Cl | CH$_2$C$_6$H$_5$ | 0 | 43.6 | −0.9 |
| Tolbutamide | | | | 54.1** | 52.4** |

*Significantly different from the control (p< 0.05)
**Significantly different from the control (p< 0.01)

2. Duration of the action of the compound 4

In order to reconfirm the effectiveness of the compounds of the present invention, more detailed examinations were performed on the most representative compound (compound of the Example 4 abbreviated hereinafter as the compound 4). The compound 4 suspended in 1% CMC was orally administered in a dose of 50 mg/kg to the fasted and glucose-loaded rats according to the preceding screening test, and the blood glucose levels at 2, 4 and 6 hours after the administration were determined by the method of Momose.

The results were shown in Table 2. Hypoglycemic effect of the compound 4 appeared to be more durable than that of tolbutamide.

Table 2

| | | | Duration of action of the compound 4 Blood glucose (mg% ± SE) | | | |
|---|---|---|---|---|---|---|
| Compounds | Dose (mg/kg) | No. of animal | before administration | 2 hours | 4 hours | 6 hours |
| Control | 0 | 8 | 85.2 ± 2.7 | 78.8 ± 4.6 | 85.0 ± 3.3 | 88.7 ± 3.5 |
| compound 4 | 50 | 8 | 85.6 ± 3.2 | 50.9 ± 1.2** | 63.1 ± 3.0** | 74.0 ± 1.6* |
| Tolbutamide | 50 | 8 | 86.2 ± 2.1 | 44.7 ± 5.0** | 60.4 ± 5.4** | 80.7 ± 5.4 |

*Significantly different from the control (p< 0.05)
**Significantly different from the control (p< 0.01)

3. Relationships between doses and reducing activity of the compound 4

The compound 4 and tolbutamide were orally administered to the fasted and glucose-loaded rats in various doses. As shown in Table 3, the compound of the present invention significantly reduced the blood glucose level even at the dose of 1.14 mg/kg. Tolbutamide, on the other hand, was not potent at low doses.

Table 3

Relationships between doses and reducing activity of blood sugar of rats administered the compound 4

| Compounds | Dose (mg/kg) | No. of animal | Blood glucose (mg% ± SE) | Reduction % from control |
|---|---|---|---|---|
| Control | 0 | 7 | 91.1 ± 3.2 | 0 |
| Compound 4 | 0.56 | 7 | 77.5 ± 6.6 | 14.9 |
| Compound 4 | 1.14 | 7 | 73.4 ± 6.4** | 19.4 |
| Compound 4 | 3.38 | 7 | 72.3 ± 4.1** | 20.6 |
| Compound 4 | 6.75 | 7 | 69.2 ± 7.8* | 24.0 |
| Compound 4 | 12.5 | 7 | 59.4 ± 4.0** | 34.8 |
| Compound 4 | 25 | 7 | 49.7 ± 2.8** | 45.4 |
| Compound 4 | 50 | 6 | 54.2 ± 2.9** | 40.5 |
| Tolbutamide | 6.75 | 6 | 87.6 ± 6.5 | 3.8 |
| Tolbutamide | 12.5 | 6 | 92.4 ± 3.5 | −1.4 |
| Tolbutamide | 25 | 6 | 73.5 ± 5.0* | 19.3 |
| Tolbutamide | 50 | 7 | 47.4 ± 3.4** | 48.0 |

*Significantly different (p< 0.05)
**Significantly different (p<0.01)

4. Hypoglycemic effect of the compound 4 in alloxan diabetic rats

Alloxan diabetic rats were obtained as follows. Namely, 2.5% fresh solution of alloxan (50mg/kg) was injected into the tail vein of male rats, and the rats were daily injected with insulin (1–4 units/day) from the 7th day after the administration of alloxan. The alloxan diabetic rats which were survived for more than 2 months with daily injection of insulin were used. The alloxan diabetic rats were fasted for 24 hours after the last treatment with insulin, and then the compound of the present invention was orally administered. The blood glucose levels were determined by the micro method of Momose before and 2, 4 and 6 hours after the administration.

Since the pancreatic β cells of the Langerhans' islands were destroyed by alloxan, tolbutamide could not exert its hypoglycemic effect in the alloxan diabetic rats. On the other hand, hypoglycemic effect of the compound 4 could be observed, and it lasted so longer than that of phenformin (phenethylbiguanide) as to be potent even at 6 hours after the administration (Table 4).

Table 4

Reducing effect of the compound 4 on blood sugar of alloxan diabetic rats

| Compounds | Dose (mg/kg) | No. of animal | before administration | Blood glucose (mg% ± SE) 2 hours | 4 hours | 6 hours |
| --- | --- | --- | --- | --- | --- | --- |
| Control | 0 | 7 | 374.5 ± 34.9 | 353.7 ± 35.4 | 294.5 ± 34.2 | 184.2 ± 22.4 |
| Compound 4 | 100 | 7 | 352.1 ± 31.6 | 267.6 ± 34.3** | 172.4 ± 35.1** | 97.8 ± 13.4** |
| Phenformin | 100 | 7 | 368.7 ± 31.3 | 262.2 ± 43.3* | 196.0 ± 48.9 | 133.7 ± 29.3 |

*Significantly different ($p < 0.05$)
**Significantly different ($p < 0.01$)

5. Hypoglycemic effect of the compound 4 in adrenalectomized rats

The rats were adrenalectomized (both left and right adrenal glands) and were bred for 6–7 days by using 1% saline solution as for drinking water. The adrenalectomized rats were then fasted for 16–18 hours prior to the experiment. Glucose loading (100 mg/150g body weight) was performed by a subcutaneous administration of glucose solution on the back of the rats. Immediately after the glucose loading, the compound 4 suspended in 1% CMC was orally administered. Two hours after the oral administration, blood was obtained from the vena cava candalis of the rats under anesthesia with sodium pentobarbital. Blood glucose level was determined by the method of Momose.

As shown in Table 5, the compound 4 significantly reduced the blood glucose level even at low dose of 0.125 mg/kg.

Table 5

Reducing effect of the compound 4 on blood glucose of adrenalectomized rats

| Compounds | Dose (mg/kg) | No. of animal | Blood glucose (mg % ± SE) | Reduction % from control |
| --- | --- | --- | --- | --- |
| Control | 0 | 7 | 78.8 ± 3.8 | 0 |
| Compound 4 | 0.125 | 6 | 37.9 ± 5.5** | 51.9 |
| Compound 4 | 0.25 | 6 | 23.3 ± 4.0** | 70.4 |
| Compound 4 | 0.50 | 6 | 17.8 ± 3.6** | 77.5 |
| Compound 4 | 1.0 | 7 | 12.9 ± 1.4** | 83.6 |
| Compound 4 | 2.0 | 6 | 14.5 ± 3.2** | 81.6 |
| Compound 4 | 4.0 | 7 | 14.6 ± 2.9** | 81.6 |
| Tolbutamide | 15 | 6 | 45.7 ± 7.3** | 42.0 |
| Tolbutamide | 30 | 8 | 16.4 ± 2.1** | 79.2 |
| Tolbutamide | 60 | 7 | 9.5 ± 0.6** | 87.9 |

**Significantly different from the control ($p < 0.01$)

The compound 4 (4 mg/kg) also exerted its hypoglycemic activity on elevated blood glucose levels in adrenalectomized rats induced by subcutaneous administration of adrenalin (50 mg/kg) or intravenous injection of hydrocortisone acetate. The compound 4 was particularly effective against the hyperglycemia induced by adrenalin.

6. Effect on the serum free fatty acids (FFA) level in non-diabetic rats

The rats were fasted for 16–18 hours, and those weighing 130–160g were used. The compound 4 suspended in 1% CMC was orally administered to the fasted rats, and at 90 minutes after administration blood was drawn from the pulmonary vena cava under anesthesia with sodium pentobarbital. The blood glucose level was determined by the method of Momose, and the serum FFA level was determined by the method of Itaya and Ui as described in J. Lipid Res., 6, 16 (1965), respectively.

As shown in Table 6, the compound 4 and tolbutamide significantly lowered the blood glucose level. The compound 4 was more effective than tolbutamide in lowering the serum FFA level. Phenformin did not lower the blood glucose and serum FFA levels in this experiment.

Table 6

Suppression of the serum FFA levels in normal rats

| Drugs | Dose (mg/kg) | No. of animals | Blood glucose level (mg/dl) | Serum FFA level ($\mu$ Eq/dl) |
| --- | --- | --- | --- | --- |
| Control | 0 | 10 | 116.7 ± 6.1 | 49.6 ± 12.8 |
| Compound 4 | 100 | 10 | 66.5 ± 6.0** | 17.4 ± 5.8** |
| Tolbutamide | 100 | 10 | 57.7 ± 12.1** | 30.8 ± 15.6** |
| Phenformin | 100 | 10 | 103.0 ± 6.9 | 59.8 ± 18.0 |

**Significantly different from the control ($p < 0.01$)

Further experiment was performed to clarify the effectiveness of the compound 4 on the serum FFA. Blood samples were taken at 0.5, 1, 2, 4 and 6 hours after an oral administration of 50 mg/kg to the fasted rats and the serum FFA levels were determined. As shown in FIG. 1, the compound of the present invention markedly lowered the FFA level, and this effect could be observed at 6 hours after. Contrarily, tolbutamide and sodium glymidine resulted in only a slight suppression.

7. Effect of the compound 4 orally administered for 10 days on the blood glucose and serum FFA levels in non-diabetic rats The compound suspended in 1% CMC was orally administered once a day for 10 days to healthy rats weighing 140–160g. The rats were fasted for 16–18 hours prior to the last administration. Blood samples were taken at 90 minutes after the last administration, and the blood glucose and serum FFA levels were determined, respectively. As shown in Table 7, the compound 4 significantly lowered the serum FFA level even at a low dose (0.8mg/kg/day) which was not enough to exhibit a potent hypoglycemic effect.

Table 7

Effects on the blood glucose and serum FFA levels in normal rats administered for 10 consecutive days

| Drugs | Dose mg/kg | No. of animals | Blood glucose levels (mg/dl) | Serum FFA levels ($\mu$ Eq/dl) |
|---|---|---|---|---|
| Control | 0 | 8 | 94.9 ± 3.6 | 73.8 ± 5.4 |
| Compound 4 | 0.8 | 6 | 81.6 ± 4.8* | 46.8 ± 5.1** |
| Compound 4 | 3.1 | 8 | 74.4 ± 6.6* | 35.9 ± 2.9** |
| Compound 4 | 12.5 | 7 | 74.8 ± 3.9** | 27.1 ± 1.5** |
| Compound 4 | 50.0 | 8 | 69.9 ± 6.7** | 27.9 ± 1.5** |
| Tolbutamide | 50.0 | 8 | 33.6 ± 6.3** | 45.1 ± 2.7** |

*Significantly different from the control ($p < 0.05$)
**Significantly different from the control ($p < 0.01$)

8. Effects on the serum FFA and other lipids levels in alloxan diabetic rats

The alloxan diabetic rats which were prepared and then preserved for 6 months with insulin as described in the previous experiment were used. When the compound 4 was orally administered in doses 12.5 and 100 mg/kg to the alloxan diabetic rats, the serum FFA level was drastically decreased within 1.5 hours, and it was still more lowered even at 5 hours later. Tolbutamide and phenformin, on the other hand, had no suppressive effect on the serum FFA level in the alloxan diabetic rats. When the compound 4 was orally administered for 10 days to the alloxan diabetic rats, the serum FFA, cholesterol and triglyceride levels were significantly reduced. Phenformin, on the contrary, could not reduce the lipid levels, but rather increased the serum FFA and triglyceride levels.

Table 8

Effects on the serum lipids levels in alloxan-diabetic rats administered for 10 consecutive days

| Drugs | Dose (mg/kg) | No. of animals | FFA $\mu$ Eq/dl serum | Cholesterol mg/dl serum | Triglyceride mg/dl serum |
|---|---|---|---|---|---|
| Control |  | 8 | 64.8 ± 10.0 (100) | 59.4 ± 3.8 (100) | 55.1 ± 6.9 (100) |
| Compound 4 | 100 | 8 | 28.5 ± 7.6* (44.0) | 46.1 ± 2.9* (77.6) | 22.1 ± 4.6** (40.1) |
| Phenformin | 100 | 7 | 89.9 ± 16.4 (138.7) | 63.5 ± 5.4 (106.9) | 84.8 ± 14.3 (153.9) |

*Significantly different from the control ($p < 0.05$)
**Significantly different from the control ($p < 0.01$)

9. Effects of the compound 4 on the blood glucose and serum FFA levels in alloxan diabetic rats loaded with much quantity of glucose Respective dose of the compound 4 (12.5 and 100 mg/kg) together with 2g/kg of glucose was orally administered to the alloxan diabetic rats. The blood glucose and serum FFA levels were significantly lowered at 3 hours after the administration ($p < 0.005$). Phenformin (100mg/kg), on the other hand, significantly elevated the serum FFA level ($p < 0.05$). Tolbutamide and sodium glymidine exhibited no hypoglycemic effect in the alloxan diabetic rats.

10. Hypoglycemic effect of the compound 4 in streptozotocindiabetic rats

The rats were fasted for 16 hours, and then streptozotocin was intravenously injected in a dose of 65 mg/kg. Oral administration of the compound 4 was performed at 48 hours after the injection of streptozotocin. Blood samples were taken at 4 hours after the oral administration, and the blood glucose level in each sample was determined.

As shown in Table 9, the compound 4 markedly reduced the blood glucose level. Tolbutamide and phenformin, however, did not have a potent hypoglycemic activity in the steptozotocininduced diabetes.

Table 9

Effects on the blood glycose level in streptozotocin-diabetic rats

| Drugs | Dose (mg/kg) | No. of animals | Blood glucose level | | |
|---|---|---|---|---|---|
| | | | Before (mg %) | 4 hours (mg %) | % of inhibition |
| Control |  | 10 | 412.3 ± 10.9 | 340.6 ± 9.9 | 83.3 ± 3.6 |
| Compound 4 | 6.25 | 10 | 425.3 ± 10.5 | 263.2 ± 26.6* | 61.9 ± 6.2* |
| Compound 4 | 25 | 9 | 415.8 ± 12.2 | 251.2 ± 21.8*** | 59.8 ± 3.8**** |
| Compound 4 | 100 | 10 | 411.5 ± 16.9 | 231.4 ± 33.3** | 54.3 ± 6.4*** |
| Tolbutamide | 100 | 10 | 413.9 ± 10.2 | 327.8 ± 11.3 | 79.4 ± 2.7 |
| Phenformin | 100 | 9 | 417.1 ± 14.3 | 330.9 ± 10.6 | 79.9 ± 2.9 |

Significantly different from the control (*$p < 0.02$, $p < 0.01$, *$p < 0.005$ and ****$p < 0.001$)

11. Effect of the compound 4 on the liver glycogen level in rats loaded with glucose The rats were fasted for 16 – 18 hours, and then the compound 4 suspended in 40% glucose solution was orally administered (5 ml/kg of the suspension per body weight). Glycogen content in the liver was determined at 3 hours after the administration. Consequently, the compound 4 significantly reduced the liver glycogen level (p<0.001). On the other hand, neither tolbutamide or pnenformin exerted such effect.

12. Synergistic effect on the insulin activity

The blood glucose levels in the non-diabetic rats were respectively determined after a subcutaneous injection of insulin (0.1 unit/kg), after an oral administration of the compound 4 (25 mg/kg), and after simultaneous administrations of insulin and the compund 4. The combined use of insulin and the compound 4 was more effective to reduce the blood glucose level than the individual administration. With respect to tolbutamide, combined use with insulin was not more effective than the administration of tolbutamide alone.

13. Acute toxicity

Even when the oral dose of the compound 4 was increased up to the maximum dose (about 17g/kg) technically possible to administer, no mice or rats suffered death. Growth of the animals were not influenced, and no effect of the compound was exhibited on the central nervous system. Thus, the toxicity of the present compound was considered to be extremely low.

Based on the results of pharmacological examinations specified above, it was concluded that the new compounds of this invention were extremely useful compounds. The novel compounds of this invention exhibited potent hypoglycemic effects even in the alloxan-induced and also in the streptocin-induced diabetes, which are very important because diabetes mellitus is well-known to be an abnormal metabolic state due to an insufficiency of insulin activity. Furthermore, the novel compounds of this invention have so outstanding properties that they improve not only carbohydrate metabolism but also lipid metabolism.

EXAMPLE 1

Synthesis of 1-(N-benzenesulfonyl-β-alanyl)-3,5-dimethylpyrazole

A solution of N-benzenesulfonyl-β-alanine hydrazide (10 g) and acetylacetone (5 g) in ethanol (50 ml) was refluxed for 3 hr. The reaction mixture was poured into water (150 ml). After cooling, the precipitated crystals were separated from the solution by filtration. After drying, the crude product was obtained (12.5g, 99%). Recrystallization from ethanol gave 7.1 g of pure product, melting point 113°–115° C. Yield 56%.

| Analysis, | | | |
|---|---|---|---|
| Calcd for $C_{14}H_{17}O_3SN_3$: | C, 54.72; | H, 5.58; | N, 13.68 |
| Found: | C, 54.74; | H, 5.52; | N, 13.89. |

EXAMPLE 2

Synthesis of 1- { N-[p-(2-acetaminoethyl)benzenesulfonyl]-β-alanyl } -3,5-dimethylpryrazole N-[p-(2-Acetaminoethyl)benzensulfonyl]-β-alanine hydrazide was worked up with the same procedure as shown in example 1, with acetylacetone to prepare 1- { N-[p-(2-acetaminoethyl)benzenesulfonyl]-β-alanyl } -3,5-dimethylpyrazole. Recrystallization from 5% methanol gave pure product, melting point 127°–128° C. Yield 60%.

| Analysis, | | | |
|---|---|---|---|
| Calcd for $C_{18}H_{24}O_4SN_4$: | C, 54.78; | H, 6.17; | N, 14.28 |
| Found: | C, 54.78; | H, 5.97; | N, 14.12. |

EXAMPLE 3

Synthesis of 1- { N- { p-[2-(2-pyrazinecarbonylamino)ethyl]benzenesulfonyl } -β-alanyl } -3,5-dimethylpyrazole N- { p[2-(2-Pyrazinecarbonylamino)ethyl]benzenesulfonyl } -β-alanine hydrazide was worked up with the same procesure as shown in example 1, with acetylacetone to prepare 1- { N- { p-[2-(2-pyrazinecarbonylamino)ethyl]ethyl]benzenesulfonyl } -β-alanyl } -3,5-dimethylpyrazole. Recrystallization from 50% methanol gave pure product, melting point 154°–156° C. Yield 51%.

| Analysis, | | | |
|---|---|---|---|
| Calcd for $C_{21}H_{24}O_4SN_6$: | C, 55.25; | H, 5.30; | N, 18.41 |
| Found: | C, 55.30; | H, 5.28; | N, 18.31. |

EXAMPLE 4

Synthesis of 1-(N-p-chlorobenzenesulfonyl-glycyl)-3,5-dimethylpyrazole

N-p-Chlorobenzenesulfonylglycine hydrazide was worked up with acetylacetone to prepare 1-(N-p-chlorobenzenesulfonyl-glycyl)-3,5-dimethylpyrazole. Recrystallization from ethanol gave pure product, melting point 135°–136° C. Yield 60.3%.

| Analysis, | | | |
|---|---|---|---|
| Calcd for $C_{13}H_{14}O_3N_3SCl$: | C, 47.64; | H, 4.31; | N, 12.82 |
| Found: | C, 47.47; | H, 4.28; | N, 13.06 |

EXAMPLE 5

Synthesis of 1- { N-[p-(2-acetaminoethyl)-benzenesulfonyl]-glycyl } -3,5-dimethylpyrazole To a solution of N-[p-(2-acetaminoethyl)benzenesulfonyl]-glycine hydrazide (6.28 g) and acetylacetone (2.0 g) in ethanol (150 ml) was added acetic acid (2.0 ml). The mixture was refluxed for 2 hrs. The reaction mixture was concentrated under reduced pressure. The residue was dissolved in $CH_2Cl_2$. The solution was washed with 5% aq. $K_2CO_3$, dried over $Na_2SO_4$ and concentrated under reduced pressure. The crude product was obtained (7.52 g, 92.4%). Recrystallization from ethanol gave 4.27 g of pure product, melting point 136°–138° C. Yield 53.9%.

| Analysis, | | | |
|---|---|---|---|
| Calcd for $C_{17}H_{22}N_4O_4S$; | C, 53.97; | H, 5.82; | N, 14.81 |
| Found: | C, 54.14; | H, 5.83; | N, 14.58. |

EXAMPLE 6

Synthesis of 1- { N-[p-(2-ethoxycarbonylaminoethyl)benzenesulfonyl]-glycyl } -3,5-dimethylpyrazole N-[p-(2-Ethoxycarbonylaminoethyl)benzenesulfonyl]-glycine hydrazide was worked up with the same procedure as shown in example 5, with acetylacetone and acetic acid to prepare 1-{ N-[p-(2-ethoxycarbonylaminoethyl)benzenesulfonyl]-glycyl } -3,5-dimethylpyrazole. Recrystallization from ethanolwater gave pure product, melting point 126°–127° C. Yield 53.8%.

Analysis,
Calcd for $C_{18}H_{24}N_4O_5S \cdot \frac{1}{2}H_2O$: C, 51.92; H, 6.01; N, 13.46
Found: C, 51.81; H, 6.37; N, 13.45.

EXAMPLE 7

Synthesis of 1-{ N-[p-(2-ethoxycarbonylaminoethyl)benzenesulfonyl]-β-alanyl } -3,5-dimethylpyrazole N-[p-(2-Ethoxycarbonylaminoethyl)benzenesulfonyl]-β-alanine hydrazide was worked up with the same procedure as shown in example 5, with acetylacetone and acetic acid to prepare 1-{ N-[p-(2-ethoxycarbonylaminoethyl) benzenesulfonyl]-β-alanyl} -3,5-dimethylpyrazole. Recrystallization from ether-n-hexane gave pure product, melting point 107°–108° C. Yield 20.1%.

Analysis,
Calcd for $C_{19}H_{26}N_4O_5S$: C, 54.02; H, 6.20; N, 13.26
Found: C, 54.10; H, 6.44; N, 13.04.

EXAMPLE 8

Synthesis of 1-[N-(p-chlorobenzenesulfonyl)-β-alanyl]-3,5-dimethylpyrazole

N-(p-Chlorobenzenesulfonyl)-β-alanine hydrazide was worked up with the same procedure as shown in example 5, with acetylacetone and acetic acid to prepare 1-[N-(p-chlorobenzenesulfonyl)-β-alanyl]-3,5-dimethylpyrazole. Recrystallization from ethanol gave pure product, melting point 101° C. Yield 76.0%.

Analysis,
Calcd for $C_{14}H_{16}N_3O_3SCl$: C, 49.20; H, 4.72; N, 12.30
Found: C, 48.95; H, 4.69; N, 12.19.

EXAMPLE 9

Synythesis of 1-{ N-{ p-[2-(2-methoxy-5-chlorobenzoylamino)-ethyl]benzenesulfonyl } glycyl } -3,5-dimethyl-pyrazole N-{ p-[2-(2-Methoxy-5-chlorobenzoylamino)ethyl]benzenesulfonyl } glycine hydrazide was worked up with the same procedure as shown in example 5, with acetylacetone and acetic acid to prepare 1-{ N - { p-[2-(2-methoxy-5-chlorobenzoyl-amino)ethyl]-benzenesulfonyl } glycyl } -3,5-dimethylpyrazole. Recrystallization from ethanol gave pure product, melting point 117°–119° C. Yield 47.6%.

Analysis,
Calcd for $C_{23}H_{25}N_4O_5SCl$: C, 54.71; H, 4.96; N, 11.10
Found: C, 54.61; H, 5.07; N, 10.82.

EXAMPLE 10

Synthesis of 1-[N-(p-cyclohexylbenzenesulfonyl)-glycyl]-3,5-dimethylpyrazole

N-(p-Cyclohexylbenzenesulfonyl)glycine hydrazide was worked up with the same procedure as shown in example 5, with acetylacetone and acetic acid to prepare 1-[N-(p-cyclohexylbenzenesulfonyl)glycyl]-3,5-dimethylpyrazole. Recrystallization from ethanol-petroleum ether gave pure product, melting point 138° C. Yield 37.3%.

Analysis,
Calcd for $C_{19}H_{25}N_3O_3S$: C, 60.78; H, 6.71; N, 11.19
Found: C, 60.85; H, 6.86; N, 10.96.

EXAMPLE 11

Synthesis of 1-[N-(p-isobutylbenzenesulfonyl)-glycyl]-3,5-dimethylpyrazole

N-(p-Isobutylbenzenesulfonyl)glycine hydrazide was worked up with the same procedure as shown in example 5, with acetylacetone and acetic acid to prepare 1-[N-(p-isobutylbenezenesulfonyl)glycyl]-3,5-dimethylpyrazole. Recrystallization from ethanol-petroleum ether gave pure product, melting point 124° C. Yield 30.1%.

Analysis,
Calcd for $C_{17}H_{23}N_3O_3S$: C, 58.44; H, 6.64; N, 12.03
Found: C, 58.16; H, 6.72; N, 11,95.

EXAMPLE 12

Synthesis of 1-[N-(p-chlorobenzenesulfonyl)-α-phenylglycyl]-3,5-dimethylpyrazole A solution of N-(p-chlorobenzenesulfonyl)-α-phenyl-glycine hydrazide (1.7 g) and acetylacetone (2.5 g) in acetic acid (5 ml) was heated at 80° C for 30 min. The reaction mixture was concentrated under reduced pressure. The residue was dissolved in ethyl acetate. The solution was washed with 5% aq. $K_2CO_3$, dried over $Na_2SO_4$ and concentrated under reduced pressure. Recrystallization from ethanol gave 0.83 g of pure product, melting point 160° C. Yield 40.59%.

Analysis,
Calcd for $C_{19}H_{18}N_3O_3SCl$: C, 56.50; H, 4.49; N, 10.40
Found: C, 56.43; H, 4.50; N, 10.25.

EXAMPLE 13

Synthesis of 1-[N-(p-chlorobenzenesulfonyl)-alanyl]-3,5-dimethylpyrazole

N-(p-Chlorobenzenesulfonyl)alanine hydrazide was worked up with the same procedure as shown in example 12, with acetylacetone to prepare 1-[N-(p-chlorobenzenesulfonyl)-alanyl]-3,5-dimethylpyrazole. Recrystallization from ethanol-petroleum ether gave pure product, melting point 150° C. Yield 31.9%.

Analysis,
Calcd for $C_{14}H_{16}N_3O_3SCl$: C, 49,19; H, 4.75; N, 12,29

-continued

Found: C, 49.35; H, 4.86; N, 11.98.

EXAMPLE 14

Synthesis of 1-[N-(p-chlorobenzenesulfonyl)-phenylalanyl]-3,5-dimethylpyrazole

N-(p-Chlorobenzenesulfonyl)phenylalanine hydrazide was worked up with the same procesure as shown in example 12, with acetylacetone to prepare 1-[N-(p-chlorobenzenesulfonyl)phenylalanyl]-3,5-dimethyl-pyrazole. Recrystallization from ethanol-water gave pure product, melting point 137°–138° C. Yield 25.4%.

| Analysis, | | | |
|---|---|---|---|
| Calcd for $C_{20}H_{20}N_3O_3SCl$: | C, 57.47; | H, 4.82; | N, 10.05 |
| Found: | C, 57.20; | H, 4.89; | N, 9.81 |

What is claimed is:

1. A compound of the general formula

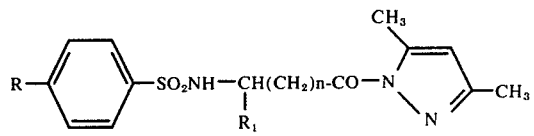

wherein
R is isobutyl, cyclohexyl or chlorine;
$R_1$ is hydrogen, methyl, phenyl or benzyl; and
$n$ is 0 or 1 when $R_1$ is hydrogen and is 0 when $R_1$ is methyl, phenyl, or benzyl.

2. A compound of the general formula

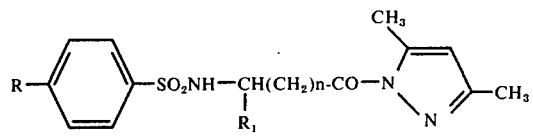

wherein
R is chlorine;
$R_1$ is hydrogen or methyl; and
$n$ is 0 or 1 when $R_1$ is hydrogen and is 0 when $R_1$ is methyl.

3. 1-(N-p-Chlorobenzenesulfonylglycyl)-3,5-dimethylpyrazole.

4. 1-[N-(p-Chlorobenzenesulfonyl)-β-alanyl]-3,5-dimethyl-pyrazole.

5. 1-[N-(p-Chlorobenzenesulfonyl)alanyl]-3,5-dimethylpyrazole.

* * * * *